United States Patent
Ishikawa et al.

(10) Patent No.: US 6,988,987 B2
(45) Date of Patent: Jan. 24, 2006

(54) GUIDE TUBE

(75) Inventors: Masahiro Ishikawa, Hino (JP); Keita Suzuki, Kokubunji (JP); Koichi Kawashima, Hachioji (JP); Tetsuya Yamamoto, Hidaka (JP); Yoshio Onuki, Hino (JP); Ryuta Sekine, Koganei (JP); Anthony Nicholas Kalloo, Glenn Dale, MD (US); Sergey Veniaminovich Kantsevoy, Silver Spring, MD (US)

(73) Assignee: Olympus Corporation, Tokyo (JP)

( * ) Notice: Subject to any disclaimer, the term of this patent is extended or adjusted under 35 U.S.C. 154(b) by 148 days.

(21) Appl. No.: 10/390,365

(22) Filed: Mar. 17, 2003

(65) Prior Publication Data

US 2003/0229296 A1    Dec. 11, 2003

Related U.S. Application Data

(60) Provisional application No. 60/365,267, filed on Mar. 18, 2002.

(51) Int. Cl.
*A61B 1/00*    (2006.01)

(52) U.S. Cl. ...................... 600/114; 600/104

(58) Field of Classification Search ........ 600/114–116, 600/104; 604/164.01
See application file for complete search history.

(56) References Cited

U.S. PATENT DOCUMENTS

| 4,686,965 | A | * | 8/1987 | Bonnet et al. | 600/104 |
|---|---|---|---|---|---|
| 4,688,554 | A | * | 8/1987 | Habib | 600/114 |
| 5,280,781 | A | * | 1/1994 | Oku | 600/114 |
| 5,297,536 | A | | 3/1994 | Wilk | |
| 5,325,845 | A | * | 7/1994 | Adair | 600/114 |
| 5,540,648 | A | * | 7/1996 | Yoon | 600/114 |
| 2001/0049497 | A1 | * | 12/2001 | Kalloo et al. | 604/164.01 |
| 2003/0083546 | A1 | * | 5/2003 | Butler et al. | 600/114 |

FOREIGN PATENT DOCUMENTS

| EP | 1 025 802 A1 | 8/2000 |
|---|---|---|
| JP | 6-54796 | 3/1994 |
| JP | 6-54798 | 3/1994 |
| JP | 2581611 | 7/1998 |

* cited by examiner

*Primary Examiner*—Beverly M. Flanagan
(74) *Attorney, Agent, or Firm*—Scully, Scott, Murphy & Presser

(57) ABSTRACT

There is provided a flexible guide tube which guides an endoscope or a therapeutic device into an abdominal cavity through the mouth and stomach to conduct an observation or a therapeutic treatment in the abdominal cavity. The guide tube includes an insertion section which has a distal end, a peripheral section, and a central axis, and which is capable of being inserted into a body through the mouth, and two expandable and shrinkable balloons arranged in the vicinity of the distal end at a predetermined distance from each other in the axial direction on the periphery of the insertion section. The predetermined distance is preferably set to 3 to 8 mm, and the length of the insertion section is preferably set to about 600 to 1000 mm.

2 Claims, 19 Drawing Sheets

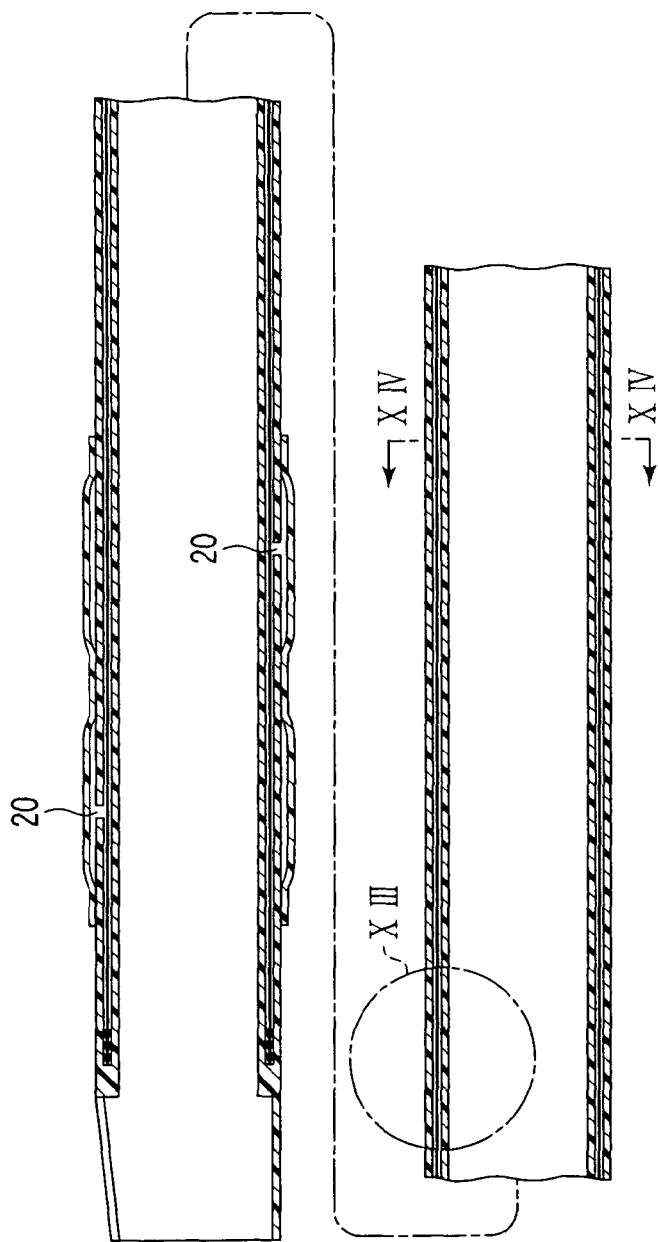
F I G. 12
F I G. 13
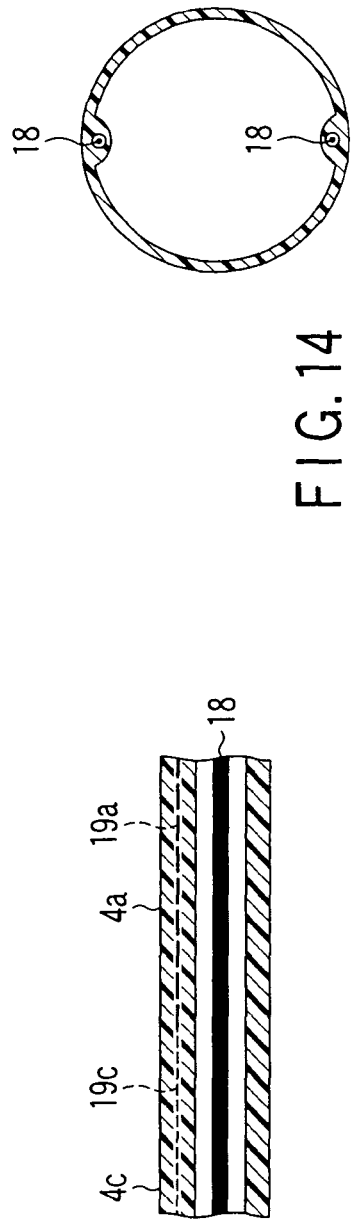
F I G. 14

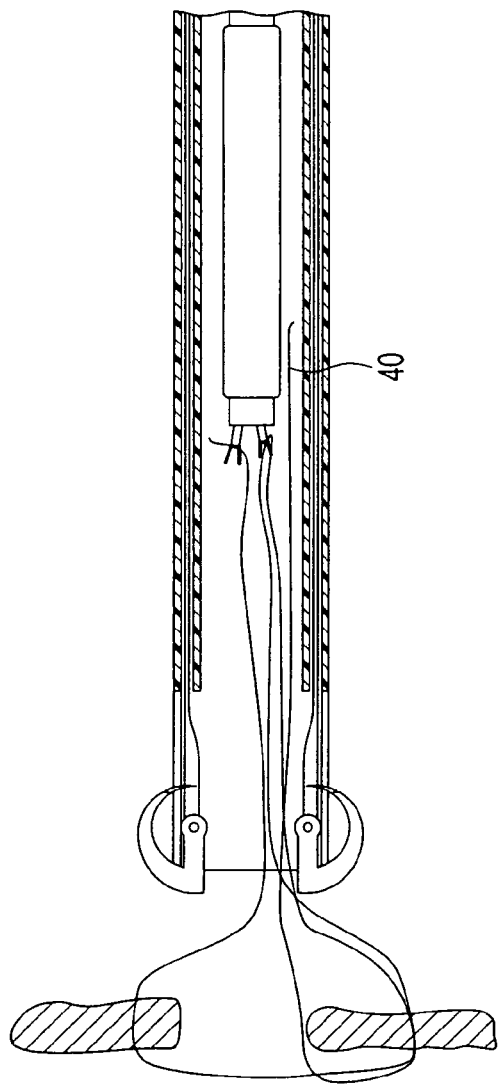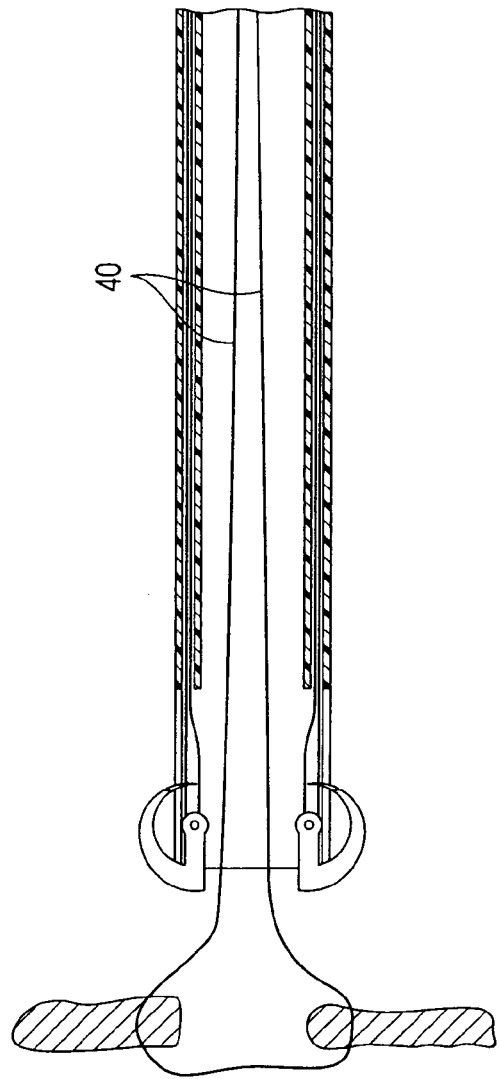
F I G. 31
F I G. 32

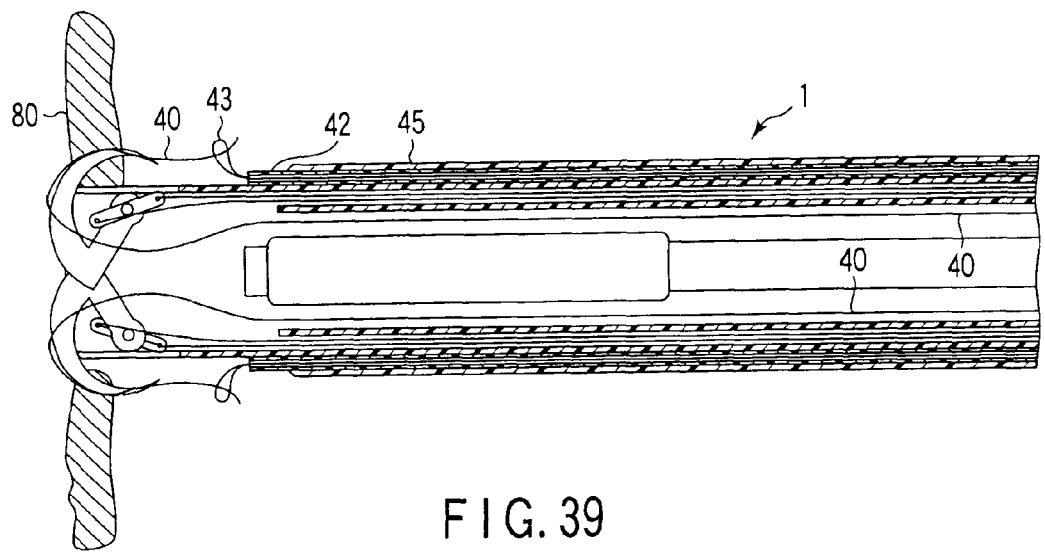
F I G. 39
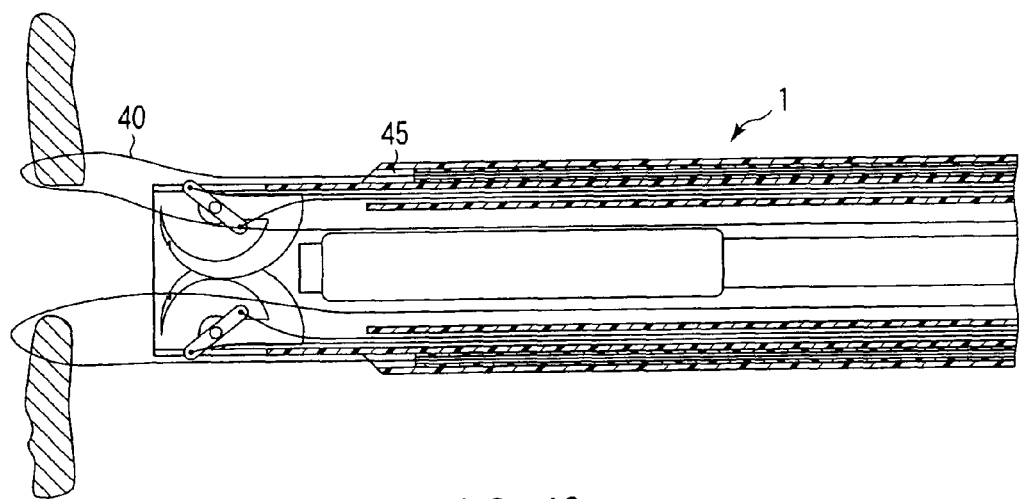
F I G. 40

GUIDE TUBE

CROSS-REFERENCE TO RELATED APPLICATIONS

This application claims the benefit of U.S. Provisional Application No. 60/365,267, filed Mar. 18, 2002.

BACKGROUND OF THE INVENTION

The present invention relates to a guide tube and, more particularly, to a guide tube to guide an endoscope or a therapeutic device into a body.

Hitherto, two methods have been generally used for a diagnosis and/or a therapeutic treatment using an endoscope. According to the first method, an endoscope is inserted through a bodily orifice, such as the mouth, anus, or urethra, to diagnose or therapeutically treat the alimentary canal, a digestive organ, or urinary organ. According to the second method, a perforation is formed in an abdominal wall on the outside of a body cavity and an endoscope is inserted through the perforation to conduct a diagnosis and a therapeutic treatment of an organ through an abdominal cavity. In the first method, since a perforation is not needed, the burden on the patient is small. However, since the therapeutic treatment is performed through a narrow tubular cavity, only a portion in the tubular cavity can be treated. In the second method, the perforation is formed in the abdominal wall and an endoscope and one or more surgical instruments are inserted through the perforation to perform therapeutic treatment. Various therapeutic treatments can be performed. However, since a perforation is formed in the abdominal wall, it takes time for the perforation to heal.

U.S. Pat. No. 5,297,536 discloses the following manipulation. According to the manipulation, a tube is inserted into the stomach through the mouth. A perforation is formed in the stomach wall by an incising instrument inserted through the tube. An endoscope is then inserted into the abdominal cavity through the perforation. A therapeutic treatment is then performed in the abdominal cavity using the endoscope. Finally, the perforation is closed.

As mentioned above, when the endoscope is inserted into the abdominal cavity through the stomach wall, it is preferable that a distal end of a guide tube guiding the endoscope be fixed to the stomach wall. This is because, if the distal end of the guide tube is dropped in the stomach, the endoscope cannot be inserted stably.

The conventional guide tube to insert the endoscope into the stomach through the mouth is intended to easily pass the endoscope through the pharynx. Accordingly, the length of the conventional guide tube is about 200 to 300 mm. On the other hand, the distance from the mouth to the pharynx is about 100 mm, the length of the esophagus is about 250 mm, and the distance from a cardia to a pylorus of the stomach is 200 to 250 mm. Accordingly, in order to guide the endoscope to the stomach wall through the mouth, a guide tube of 550 mm or longer is needed. Therefore, conventional guide tubes cannot reach the stomach wall. U.S. Pat. No. 5,297,536 does not disclose fixing the guide tube to the stomach wall.

On the other hand, European Patent No. 1,025,802 discloses a guide tube which is percutaneously inserted into the small intestine through the abdominal wall. Many methods for percutaneously fixing the guide tube to the abdominal wall have been disclosed. For example, in Jpn. Pat. Appln. KOKAI Publication No. 6-54798, an abdominal wall is sandwiched between two balloons to fix a tube to the abdominal wall. The size of each balloon is also disclosed. The balloons are effectively used for fixing the tube to the abdominal wall. However, the anatomical thickness of the stomach wall is 3 to 8 mm. Accordingly, the conventional balloons are not of an appropriate size for fixing the tube to the stomach wall, because the tube cannot be securely fixed.

Furthermore, after diagnosis or therapeutic treatment of the abdominal cavity are finished through the stomach wall, it is necessary to close the perforation in the stomach wall. The foregoing U.S. Pat. No. 5,297,536 discloses the following device. According to the device, a tube and a rubber ring are attached to the periphery of the endoscope and the perforation is closed using the rubber ring. When the closing device is used, tissue around the perforation is withdrawn into the tube, drawn into the device and ligatured by the ring. However, it is difficult to draw the area surrounding the perforation in the stomach wall into the tube, therefore the closing operation may sometimes not be performed satisfactorily.

BRIEF SUMMARY OF THE INVENTION

The present invention was arrived at after consideration of the above problems and it is an object of the present invention to provide a guide tube which is long enough to guide an endoscope and a therapeutic device through the mouth and stomach wall.

Another object of the present invention is to provide a guide tube which can be surely fixed to the stomach wall and which can guide an endoscope and a therapeutic device stably and easily.

Still another object of the present invention is to provide a guide tube which can close a perforation easily and surely.

To accomplish the above objects, according to a first aspect of the present invention, there is provided a flexible guide tube which guides an endoscope or a therapeutic device into an abdominal cavity through the mouth and stomach to conduct an observation and a therapeutic treatment in the abdominal cavity. The guide tube includes an insertion section which has a distal end, a peripheral section, and a central axis, and which is capable of being inserted into a body through the mouth; and two expandable and shrinkable balloons arranged in the vicinity of the distal end at a predetermined distance from each other in the axial direction on the periphery of the insertion section. The predetermined distance is preferably set to 3 to 8 mm, and the length of the insertion section is preferably set to about 600 to 1000 mm.

The guide tube is long enough to reach the stomach wall through the mouth and esophagus. The distance between the two balloons corresponds to the thickness of the stomach wall. Consequently, the guide tube can be fixed to the stomach wall easily and surely.

According to another aspect of the present invention, there is provided a flexible guide tube which guides an endoscope or a therapeutic device into an abdominal cavity through the mouth and stomach to conduct an observation or a therapeutic treatment in the abdominal cavity. The guide tube includes an insertion section which has a distal end and which is capable of being inserted into a body through the mouth. Each of the endoscope and the therapeutic device has a bending function, and a portion close to the distal end of the insertion section is flexible so that the endoscope or the therapeutic device can exhibit the bending function.

According to still another aspect of the present invention, there is provided a flexible guide tube to guide an endoscope or a therapeutic device into a body cavity through the mouth.

The guide tube includes an insertion section which can be inserted into a body through the mouth, the insertion section having a distal end arranged in the body and at least one lumen, through which the endoscope or therapeutic device can be inserted; a proximal end which is connected to the insertion section and is arranged on the outside of the body; a shaft which is arranged in the vicinity of the distal end in the direction perpendicular to the direction in which the longitudinal axis of the insertion section extends; a curved needle which is rotatably attached to the shaft and which has an engaging portion capable of engaging a suture therewith; and driving force transmitting member which has one end connected to the curved needle and the other end arranged at the proximal end. The distal end is capable of being fixed to a required portion in the body cavity to suture tissue by operating the driving force transmitting member on the outside of the body.

According to the guide tube of the present invention, therefore, the endoscope and the therapeutic device can be guided into the stomach wall through the mouth. Furthermore, since the guide tube can be surely fixed to the stomach wall, the endoscope and the therapeutic device can be guided stably. When the guide tube according to the present invention is used, the perforation can be closed easily and surely.

BRIEF DESCRIPTION OF THE SEVERAL VIEWS OF THE DRAWING

FIG. 12 is an enlarged sectional view of a shaft section of the guide tube in FIG. 11;

FIG. 13 is a sectional view showing an enlarged wall of the shaft section shown by a circle XIII in FIG. 12;

FIG. 14 is a cross-sectional view of the shaft section taken along line XIV—XIV in FIG. 12;

FIGS. 29 to 33 are schematic diagrams of the vicinity of the distal end of the guide tube shown in FIG. 25 in order to explain an observation or a therapeutic treatment of an abdominal cavity using the guide tube;

FIGS. 39 to 43 are schematic diagrams showing the vicinity of the distal end of the guide tube shown in FIG. 34 in order to explain an observation or a therapeutic treatment of an abdominal cavity using the guide tube.

DETAILED DESCRIPTION OF THE INVENTION

Figure 1:
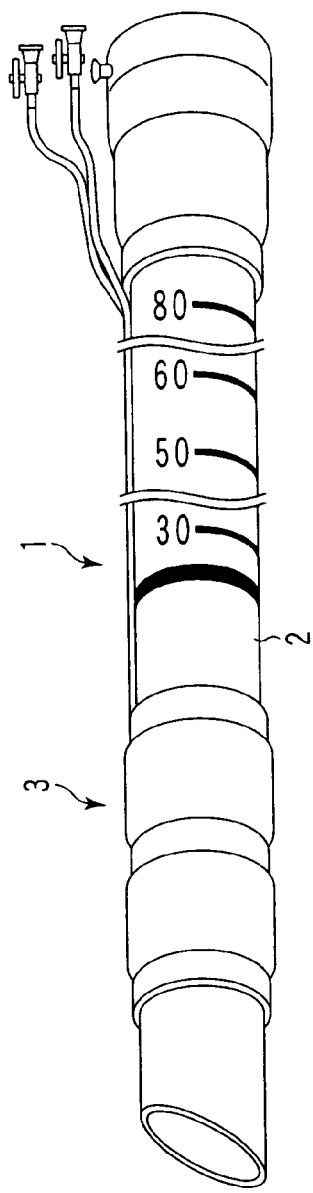
FIG. 1 is a perspective view for explaining the entire constitution of a guide tube according to a first embodiment of the present invention.
Figure 2:
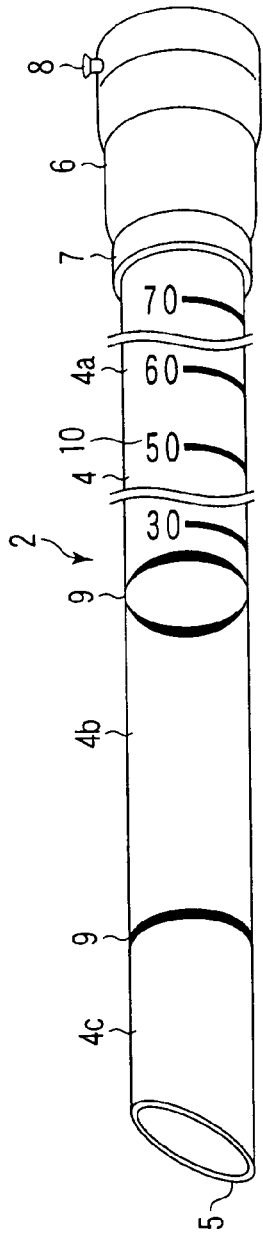
FIGS. 2 and 3 are perspective views of sections constituting the guide tube in FIG. 1.
Figure 3:
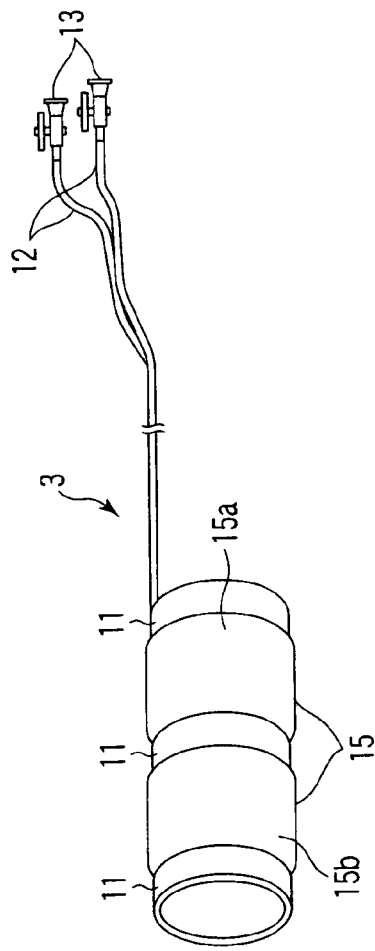
Figure 4:
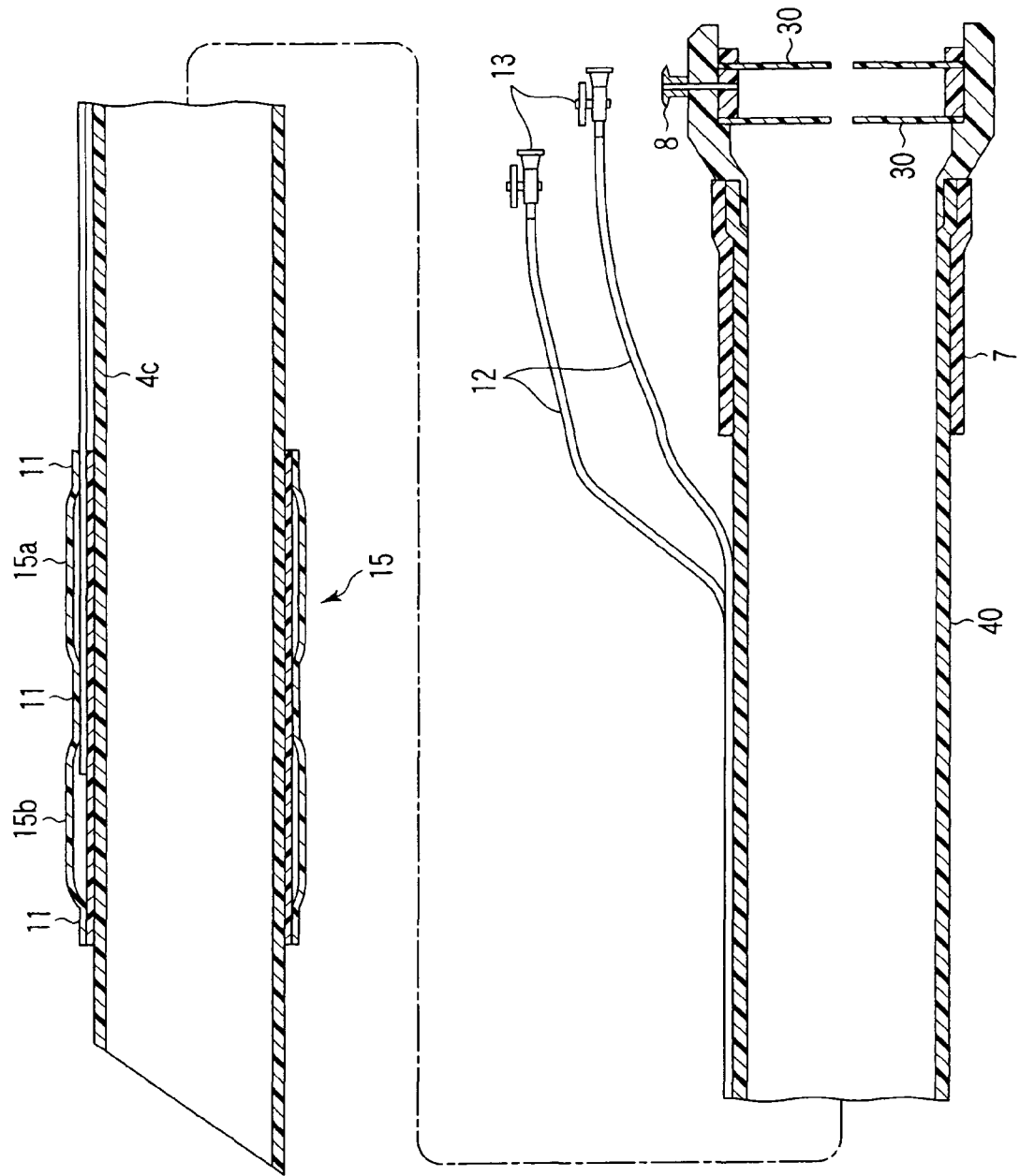
FIG. 4 is an enlarged sectional view of the guide tube in FIG. 1.

Embodiments of the present invention will now be described hereinbelow with reference to the accompanying drawings.

FIGS. 1 to 10 show a first embodiment of the present invention.

Referring to FIGS. 1 to 4, according to the present embodiment, a guide tube 1 guides an endoscope or a therapeutic device through the mouth and stomach wall into an abdominal cavity to conduct a diagnosis and a therapeutic treatment of the abdominal cavity. The guide tube 1 includes a flexible shaft section 2, which is thin and long and which can be inserted into a body cavity, and a balloon section 3 which is detachable from the periphery of the shaft section 2. The inner diameter of the balloon section 3 is formed so as to be slightly smaller than the outer diameter of the shaft section 2. The shaft section 2 is pressed into the balloon section 3, so that they can be fixed to each other. In the present embodiment, a distal end of the balloon section 3 is disposed at a distance of 20 mm from a distal end of the shaft section 2.

The shaft section 2 includes a tubular main body 4 and an operating handle 6. The tubular main body 4 has a proximal end portion 4a which is preferably made of expanded polytetrafluoroethylene (ePTFE), a transparent intermediate portion 4b which is preferably made of polyurethane, and a distal end portion 4c which is preferably made of ePTFE. The proximal end portion 4a and the intermediate portion 4b are connected by a connection, which is designated by reference numeral 9. The intermediate portion 4b and the distal end portion 4c are connected by another connection 9. Inner bores of the respective portions are coaxially connected, thereby forming one inner bore.

A scale 10 indicative of the distance from a tip 5 is arranged on the periphery of the proximal end portion 4a of the tubular main body 4. The operating handle 6 is connected to a proximal end of the proximal end portion 4a. The periphery of a connection between the proximal end portion 4a and the operating handle 6 is covered with a heat-shrinkable anti-bending member 7. When the anti-bending member 7 is heated in a state where the member is disposed around the periphery of the proximal end portion 4a, the member is shrunk to fasten the periphery of the connection. A lure type mouthpiece 8 for supplying a fluid from the external side into the inner bore is arranged in the operating handle 6. Two valves 30, which are preferably made of fluororubber, are disposed at a distance from each other in the axial direction so as to sandwich the mouthpiece 8. In the present embodiment, the distance from a distal end of the anti-bending member 7 to the tip 5 of the tubular main body 4 is set to 650 mm within a preferable range of 600 to 1000 mm and the outer diameter of the shaft section 2 is set to 17 mm. The outer diameter of the insertion section or shaft section 2 is preferably equal to or smaller than 20 mm. The shaft section 2 or tubular main body 4 has such flexibility that the endoscope inserted therethrough can be bent. Consequently, when the endoscope is inserted into the guide tube 1, the endoscope can be bent as necessary.

As a material forming the shaft section 2, in addition to the foregoing material, a material such as styrene elastomer, olefin elastomer, or silicone can also be used.

Subsequently, the balloon section 3 has an expandable and shrinkable balloon 15 which has an inner film and an outer film and which is preferably made of translucent silicone. The both ends and the intermediate portions of the inner and outer films of the balloon 15 are adhered to each other by adhering portions 11 to form two balloons 15a and 15b separated in the axial direction of the guide tube 1. Two lines 12 for supplying and/or discharging a fluid as a liquid and/or a gas to/from the balloons 15a and 15b are disposed adjacent to each other so as to extend in the same direction above the periphery of the shaft section 2. The intermediate portions of two lines 12 can also be integrated with each other. An injection port 13 is connected to a proximal end of each line 12. According to the present embodiment, when a fluid of about 40 ml is supplied, the balloons 15a and 15b expand so that each outer diameter is substantially equal to 45 mm. The outer diameter of each balloons 15a and 15b is preferably equal to or larger than 30 mm upon expansion. The adhering portion 11 in the intermediate portion forms an interval between the two balloons 15a and 15b. The length of the adhering portion in the axial direction is set to about 5 mm within a preferable range of 3 to 8 mm. When the periphery of the shaft section 2 is covered with the balloon section 3, the outer diameter of each of the balloons 15a and 15b is set to about 20 mm.

As a material of the balloon 15, in addition to the foregoing material, a material such as styrene elastomer or latex can also be used.

Subsequently, a method for fixing the endoscope guide tube 1 according to the present embodiment to the stomach wall and a diagnosis procedure in the abdominal cavity will now be described with reference to FIGS. 5 to 10.

Figure 5:
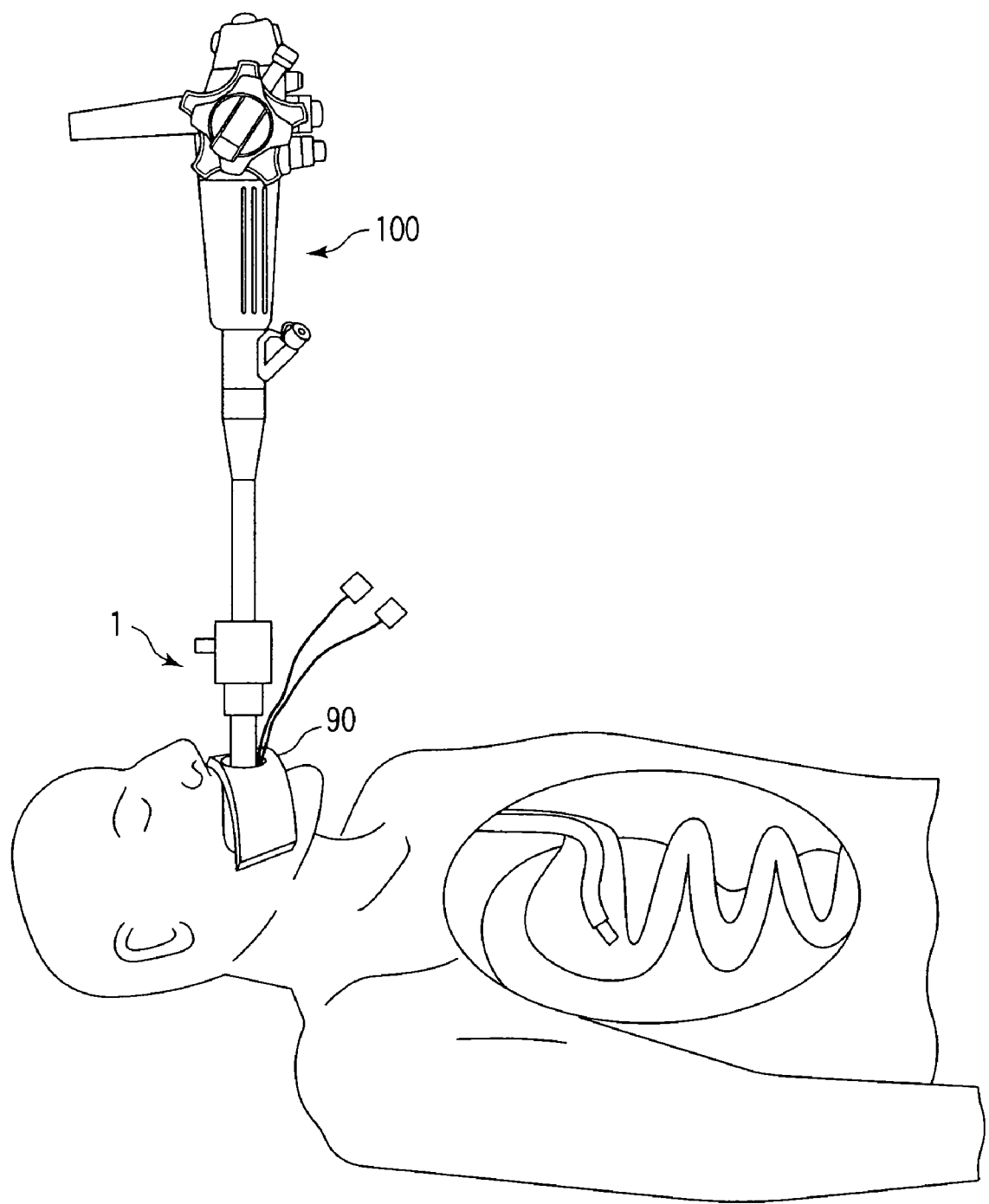
FIG. 5 is an explanatory diagram of the guide tube of FIG. 1 which is inserted together with an endoscope through the mouth.

First, a fluid is discharged from the balloons 15a and 15b to shrink the balloon section 3. In this state, for example, an endoscope 100 serving as a gastroendoscope is inserted into the inner bore of the guide tube 1. As the endoscope 100, a forward viewing type endoscope having an observation window on the surface at the distal end is preferably used. Then, as shown in FIG. 5, the guide tube 1 is inserted together with the endoscope 100 through the mouth of a patient who holds the mouthpiece 90 in their mouth, into the stomach.

Figure 6:
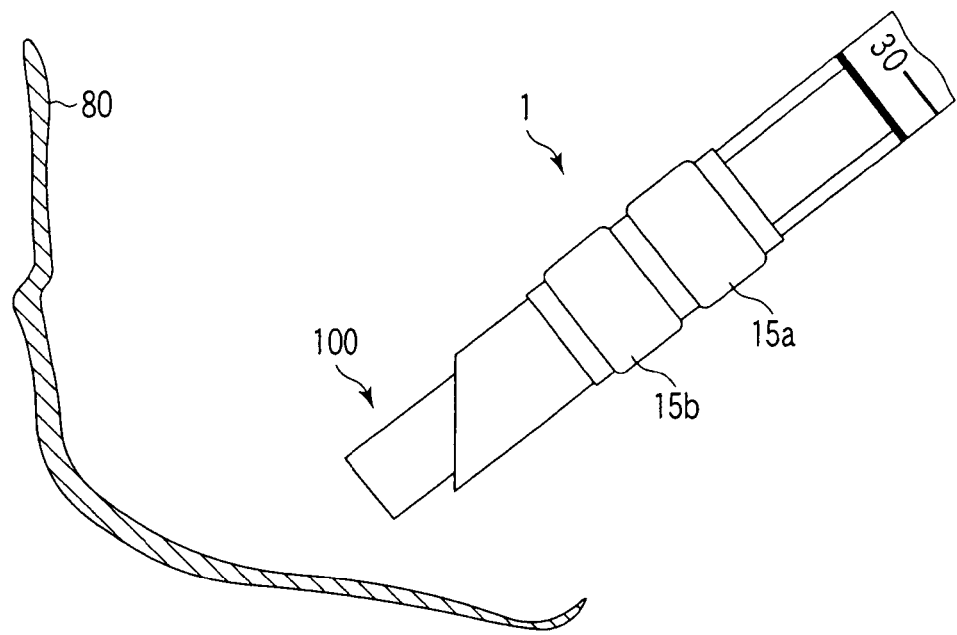
FIGS. 6 to 10 are schematic views showing the vicinity of a distal end of the guide tube of FIG. 1 in order to explain an observation or a therapeutic treatment of an abdominal cavity using the guide tube.
Figure 7:
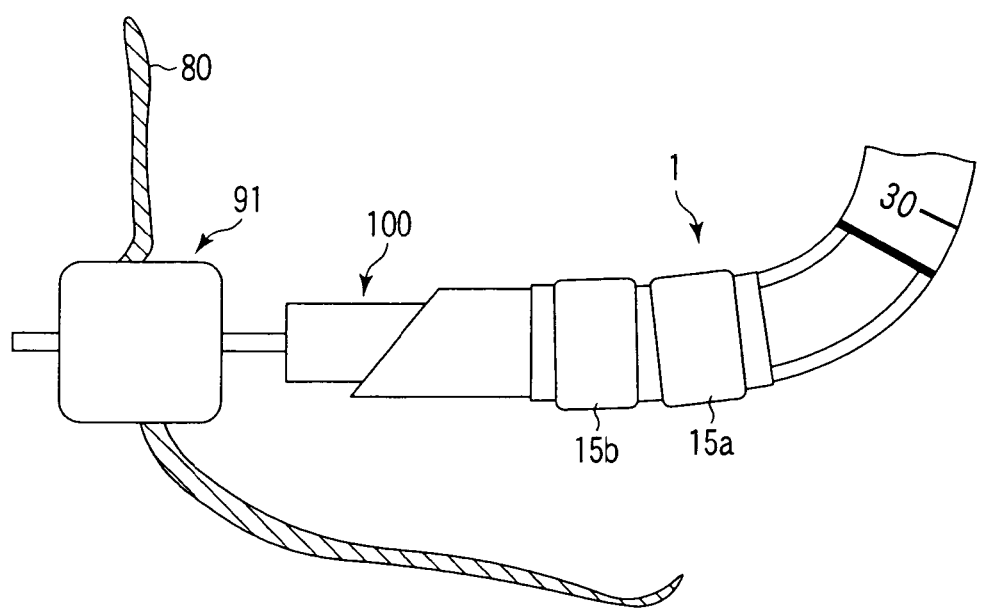

Subsequently, as shown in FIGS. 6 and 7, the bending mechanism of the endoscope 100 is operated to bend the guide tube 1 together with the endoscope 100, so that the distal end surface of the endoscope faces a required portion as a target in a stomach wall 80. Subsequently, an incising instrument (not shown) is inserted into a channel (not shown) of the endoscope 100 and is then projected from a distal end of the endoscope 100. Then, a small perforation is formed in the stomach wall 80 as a target by the incising instrument. After that, a balloon dilator 91, which is inserted through the channel of the endoscope 100 and is then projected from the distal end of the endoscope 100, is inserted into the formed perforation. The balloon dilator 91 is expanded as shown in FIG. 7 to enlarge the perforation.

Figure 8:
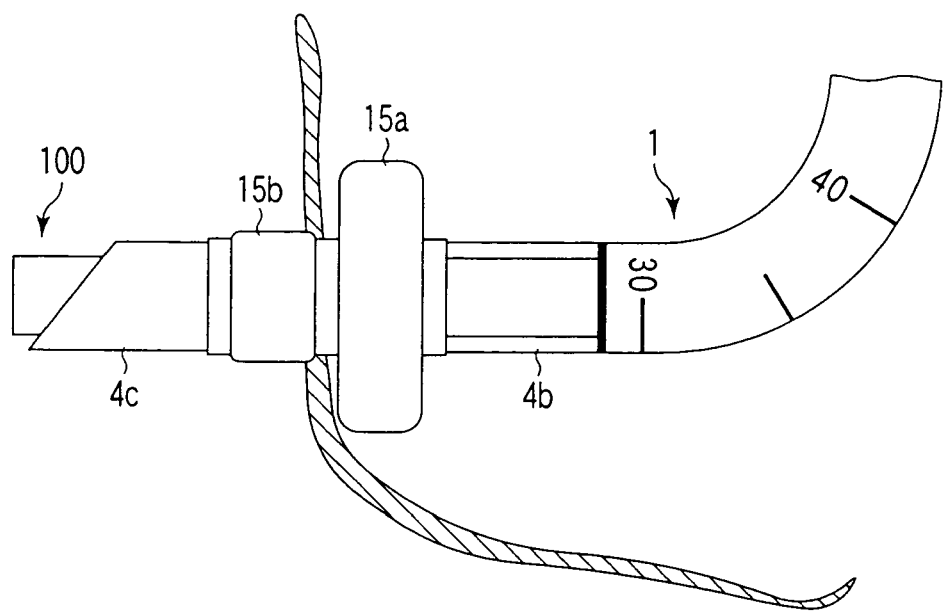

Subsequently, the guide tube 1 is advanced as shown in FIG. 8, so that the distal end of the guide tube 1 is inserted into the enlarged perforation. In this instance, the guide tube 1 is advanced on the basis of an endoscopic image obtained by the endoscope 100 and information regarding the measured insertion distance shown by the scale 10 arranged on the outer surface of the guide tube 1. Subsequently, a fluid is supplied from a syringe (not shown) attached to the mouthpiece 13 into the balloon 15a on the proximal end side to expand the balloon 15a so as to have the outer diameter of, for example, 45 mm. In this instance, the balloon 15a can also be expanded in the following manner. The distal end of the endoscope 100 is withdrawn to a position in the transparent intermediate portion 4b and, while the expanding state of the balloon 15a is confirmed in the inner bore of the guide tube 1 on the basis of the endoscopic image, the balloon 15a is expanded.

Figure 9:
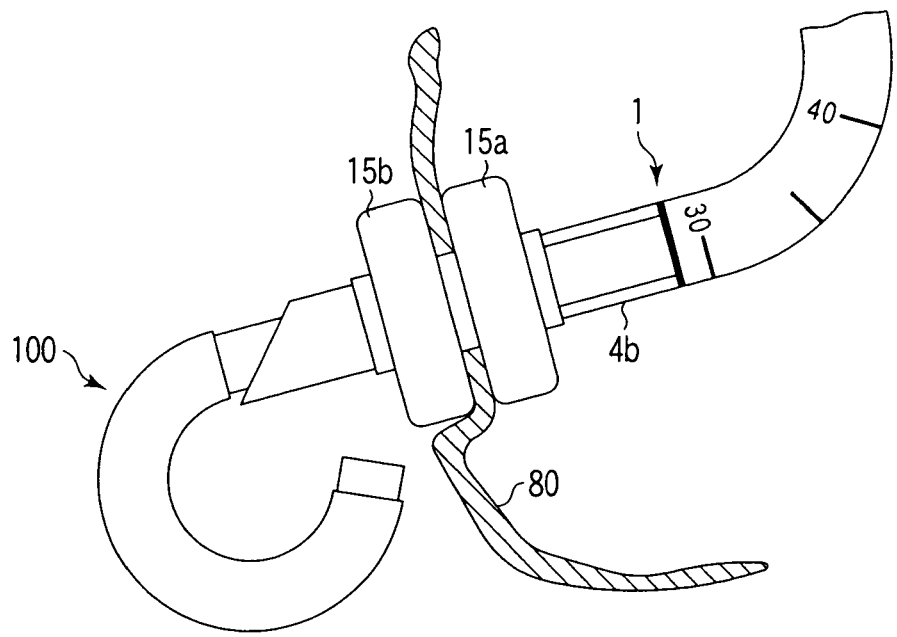
Figure 10:
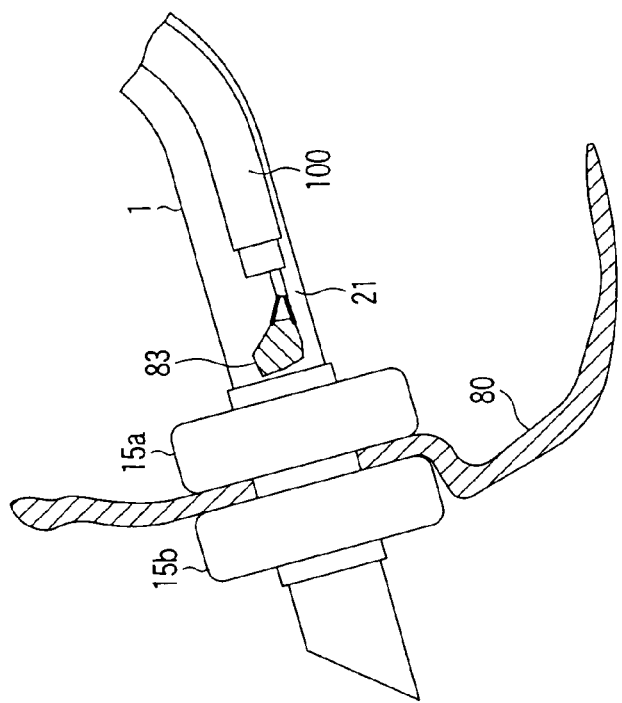

Subsequently, when the guide tube 1 is advanced as the balloon 15a is expanded, the balloon 15a is brought into contact with the stomach wall 80. The balloon 15b on the distal end side is disposed on the outside of the stomach. Referring to FIG. 9, when the balloon 15b on the distal end side is expanded, the stomach wall 80 is sandwiched between the balloon 15a on the proximal end side and the balloon 15b on the distal-end side. Consequently, the distal end of the guide tube 1 is fixed to the stomach wall 80. Subsequently, the endoscope 100 is advanced or withdrawn through the guide tube 1 as necessary, whereby a predetermined organ in the abdominal cavity is diagnosed using the endoscope 100. After that, a therapeutic forceps (not shown) is inserted into a forceps channel (not shown) of the endoscope 100 and is then projected from an opening at the distal end of the endoscope 100 to perform a therapeutic treatment. As shown in FIG. 10, a resected tissue 83 is grasped by a grasping forceps 21. The tissue 83 can be discharged from the body cavity together with the endoscope 100. When the guide tube 1 is withdrawn after the therapeutic treatment, the fluid is discharged from the balloon 15b on the distal end side to reduce the size of the balloon 15b to the original size. After the guide tube 1 is withdrawn, the perforation is closed using a closing instrument (not shown) and then the therapeutic treatment is completed.

According to the present embodiment, the guide tube 1 is long enough to reach the stomach wall through the mouth. Furthermore, since the outer diameter of the guide tube 1 is small, the guide tube 1 can be smoothly passed through the pharynx. Moreover, when the distal end of the guide tube 1 is inserted through the stomach wall, the endoscope 100 can be guided into the abdominal cavity. Further, since the interval between the two balloons 15a and 15b disposed at the distal end is 5 mm, the balloons can appropriately sandwich the stomach wall 80, so that the guide tube 1 can be fixed. Consequently, the airtightness between the stomach inner portion and the abdominal cavity can be maintained. Moreover, since the guide tube 1 has high flexibility, the guide tube 1 can be bent by bending the endoscope 100. Consequently, the guide tube 1 and the endoscope 100 can be guided to a target position. The shaft section 2 and the balloon section 3 can be detached from each other. Even when the balloon section 3 is broken, another new balloon section 3 can be attached and the guide tube 1 can be used again.

FIGS. 11 to 16 show a second embodiment of the present invention. Embodiments, which will be described below, are fundamentally similar to the foregoing first embodiment. Portions different from those in the first embodiment will be described principally. The similar references designate the similar portions as those in the first embodiment to avoid a repeated description.

Figure 11:
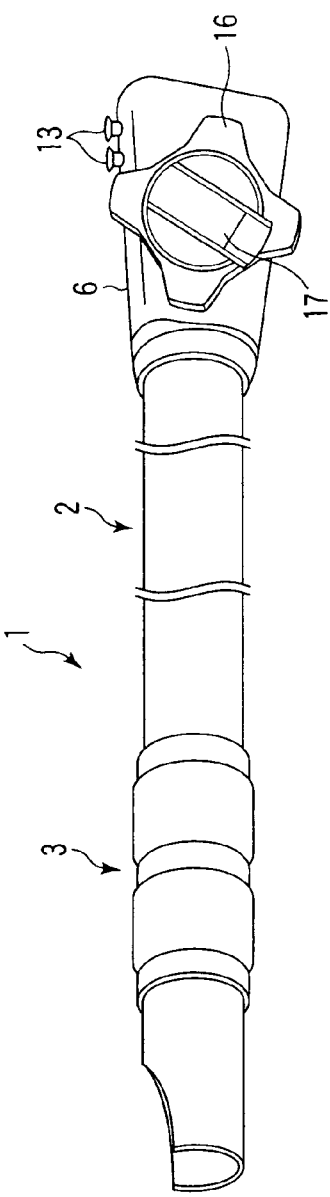
FIG. 11 is a perspective view for explaining the entire constitution of a guide tube according to a second embodiment.

According to the present embodiment, the guide tube 1 has the shaft section 2 and the balloon section 3 integrated with each other, as shown in FIG. 11. Further, the shaft section 2 includes two small lumens and one large lumen as shown in FIGS. 12 and 14. Distal ends of the two small lumens are closed in the vicinity of the distal end of the guide tube 1 and proximal ends thereof communicate with the injection port 13, respectively. The two small lumens communicate with the balloons 15a and 15b through side orifices 20 each serving as a radial bore formed in the wall of the guide tube 1. An operating wire 18 is inserted into each of the two small lumens. A distal end of the operating wire 18 is fixed to the shaft section 2 at the closed portion at the distal end of each small lumen. A proximal end of each operating wire 18 is fixed to an angle control section 16 arranged on the operating handle 6.

Referring to FIG. 13, a reinforcing layer (for example, a coil made of stainless steel) is embedded in the wall of the shaft section 2. According to the present embodiment, the reinforcing layer includes reinforcing layers 19a and 19c disposed on the proximal end portion 4a and the distal end portion 4c of the guide tube 1. The proximal-end side reinforcing layer 19a is thicker than the distal-end side reinforcing layer 19c. Generally, the flexibility of the distal end portion 4c is higher than that of the proximal end portion 4a. In this instance, the reinforcing layer can use a braided structure. As a material, a resin can be used. A thread can also be used.

The angle control section 16 is rotatably provided for the operating handle 6 at the proximal end of the shaft section 2. An angle lock section 17 which can restrict the rotating operation of the angle control section 16 is arranged adjacent to the angle control section 16.

Figure 15:
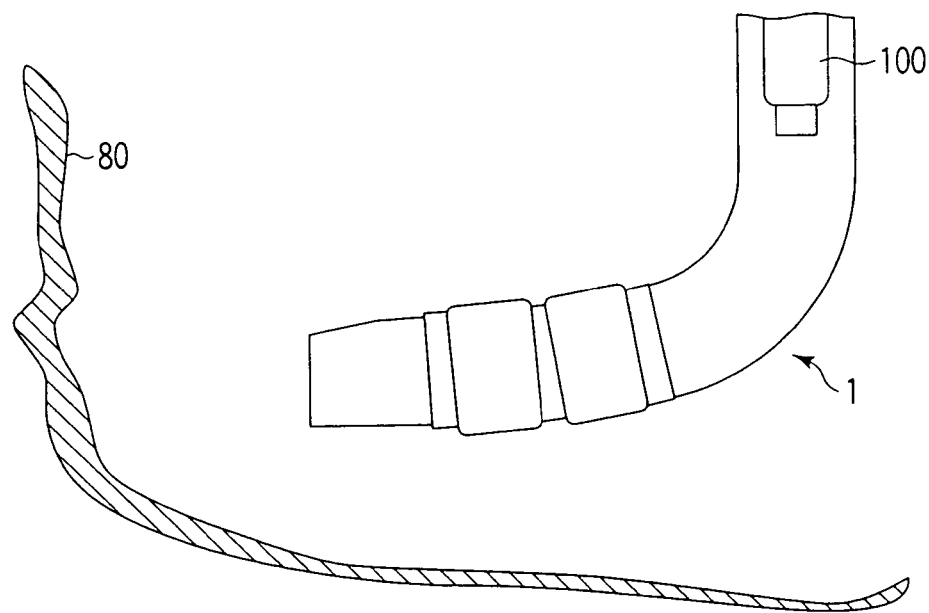
FIGS. 15 and 16 are schematic diagrams showing the vicinity of a distal end of the guide tube in FIG. 11 in order to explain an observation or a therapeutic treatment of an abdominal cavity using the guide tube.
Figure 16:
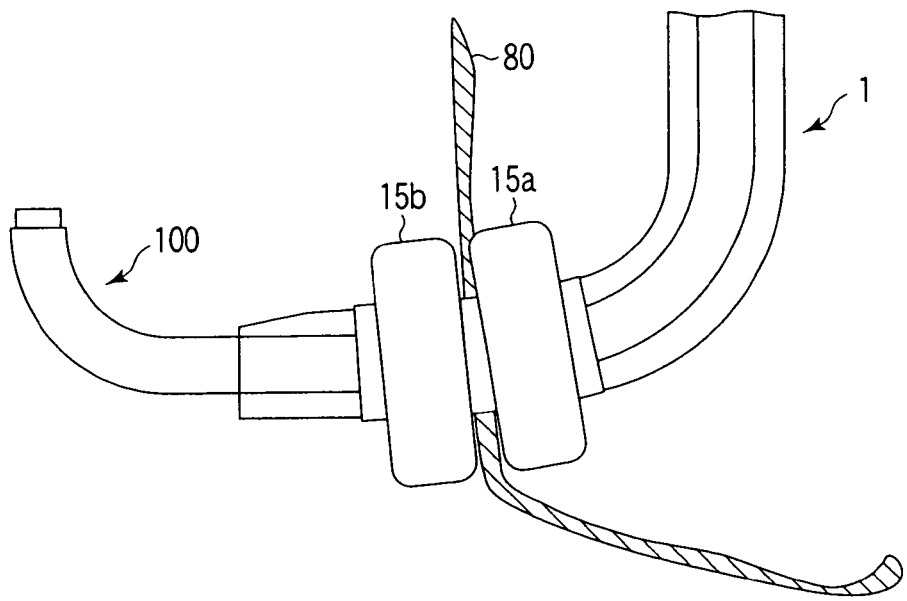
Figure 17:
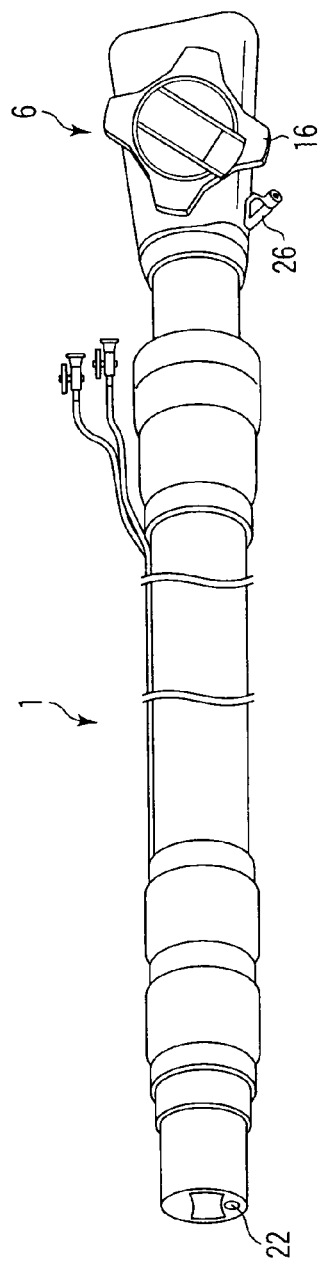
FIG. 17 is a perspective view for explaining the entire constitution of a guide tube according to a third embodiment.
Figure 18:
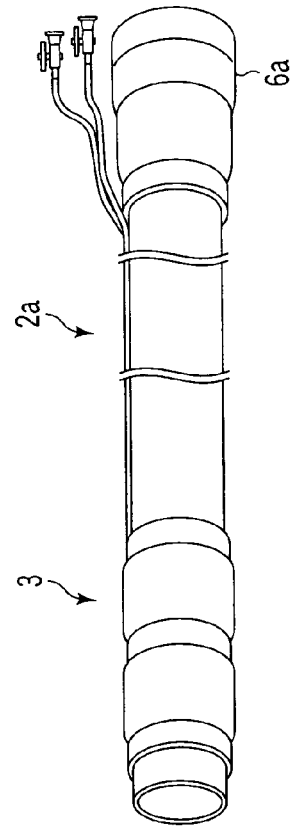
FIGS. 18 and 19 are perspective views of sections included in the guide tube in FIG. 17.
Figure 19:
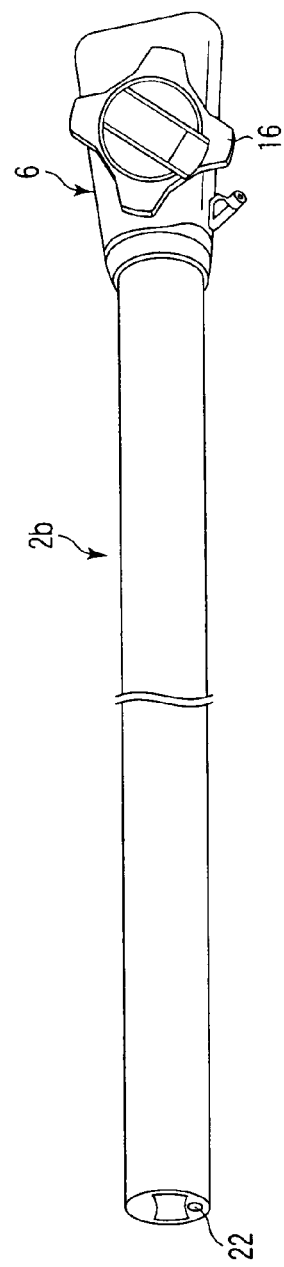
Figure 20:
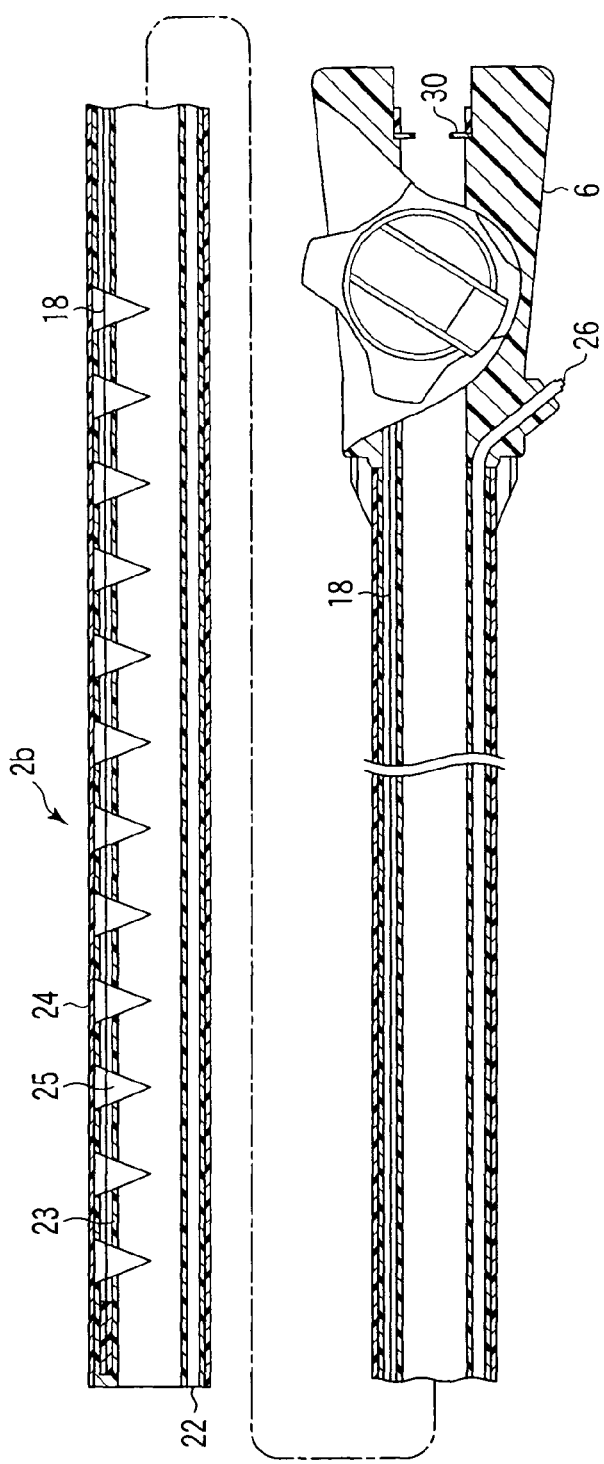
FIG. 20 is a sectional view of an inner-tube module shown in FIG. 19.
Figure 21:
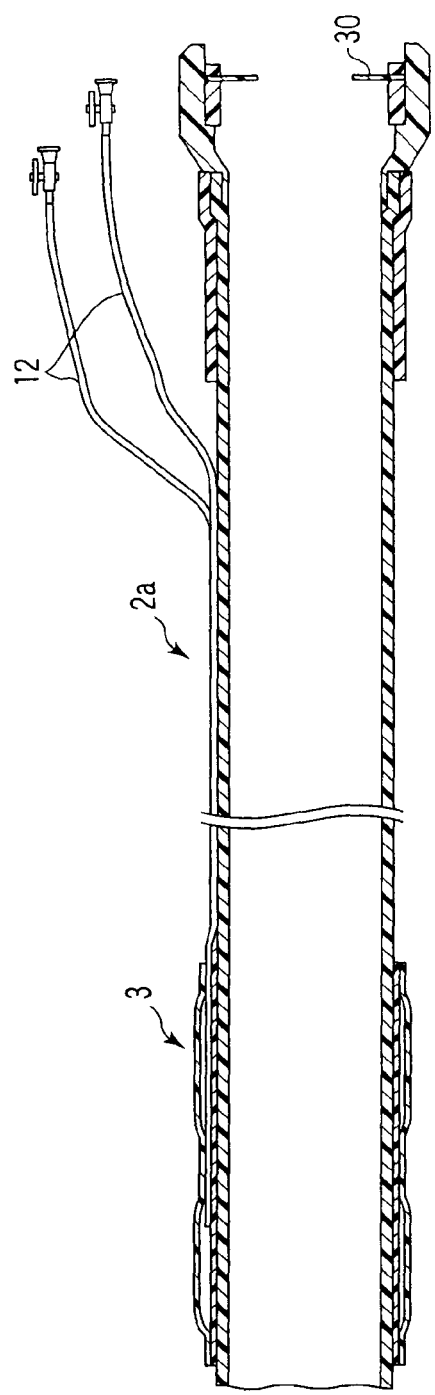
FIG. 21 is a sectional view of an outer-tube module shown in FIG. 18.

The operation different from that of the first embodiment will now be described with reference to FIGS. 15 and 16.

According to the present embodiment, after the endoscope guide tube 1 is inserted into the stomach through the mouth, the angle control section 16 is rotated to pull one of the two operating wires 18 extending so as to face each other in the radial direction toward the proximal end and extrude the other wire toward the distal end. Consequently, the shaft section 2 itself is bent as shown in FIG. 15. According to the present embodiment, in the shaft section 2, the flexibility of the area in the distal end portion 4c is higher than that of the area in the proximal end portion 4a. Accordingly, the area in the proximal end portion 4a is not bent and the area in the distal end portion 4c is bent. When the angle lock section 17 is operated so that the surface at the distal end of the guide tube 1 faces a desired portion in the stomach wall, the bent-shape of the guide tube 1 can be fixed. After that, when the endoscope 100 is advanced in the guide tube 1, the endoscope 100 is advanced so as to reach the desired portion in the stomach wall 80. The perforation and the enlargement in the stomach wall 80 and the fixing of the guide tube 1 to the stomach wall 80 are the same as those in the first embodiment. FIG. 16 shows a state where the distal end of the guide tube 1 is fixed to the stomach wall 80 and the endoscope 100 is operated in the body cavity on the outside of the stomach.

According to the present embodiment, in addition to the advantages of the first embodiment, the guide tube 1 has such a mechanism that the guide tube 1 itself can be bent. Accordingly, the guide tube 1 can be directly bent. Consequently, compared with the first embodiment in which the guide tube 1 is bent by the endoscope 100, namely, the guide tube 1 is indirectly bent, the guide tube 1 can face the desired portion with higher precision. The guide tube 1 can be held in a required bent-shape. Accordingly, even when the endoscope 100 is withdrawn from the guide tube 1, the distal end of the guide tube 1 is held substantially perpendicular to the stomach wall 80. Consequently, a load applied to the stomach wall 80 by the balloon section 3 is small and the guide tube 1 can be fixed to the stomach wall 80 more surely. Further, since the reinforcing member is embedded, the following properties of the guide tube 1 for the rotation around the longitudinal axis are improved, so that the inserting and positioning properties are raised.

According to the present embodiment, a fluid supply line to expand the balloons 15a and 15b are embedded in the shaft section 2, the outer diameter of the guide tube 1 excluding the balloon section 3 can be reduced. Compared with the guide tube 1 according to the first embodiment, higher inserting properties are obtained.

FIGS. 17 to 24 show a third embodiment of the present invention.

As shown in FIGS. 17 to 21, the guide tube 1 according to the present embodiment includes an outer-tube module 2a and an inner-tube module 2b which can be advanced or withdrawn in an inner bore of the outer-tube module 2a and which is inserted so as to hold airtightness.

The balloon section 3 is integrally connected to the outer-tube module 2a so that the distal end of the balloon section 3 is disposed at a distance of about 10 mm from a distal end of the outer-tube module 2a. An operating handle 6a in which the valve 30 (refer to FIG. 21) is arranged in the inner bore is disposed at the proximal end of the outer-tube module 2a. The overall length of the outer-tube module 2a is set to substantially 700 mm, the inner diameter thereof is set to about 18 mm, and the outer diameter thereof is set to about 20 mm.

The inner-tube module 2b has a central large-diameter inner bore, a forceps channel 22, and a small-diameter inner bore enclosing the operating wire 18 therein. The inner-tube module 2b has an inner film 23 (refer to FIG. 20) in which a plurality of slits 25 extending on the circumference of the inner-tube module 2b are formed at a distance of about 30 to 180 mm from a distal end of the inner-tube module 2b. The external surface of the inner film 23 is covered with an outer film 24 which is flexible and expandable. The respective inner bores of the inner-tube module 2b are isolated from the outside by the outer film 24. The operating handle 6 is provided at a proximal end of the inner-tube module 2b. The angle control section 16 to which the proximal end of the operating wire 18 is connected is provided on the operating handle 6. A proximal end of the forceps channel 22 is opened as a forceps opening 26 on the operating handle 6. According to the present embodiment, the overall length of the inner-tube module 2b is set to about 900 mm and the outer diameter thereof is set to about 17.5 mm.

Figure 22:
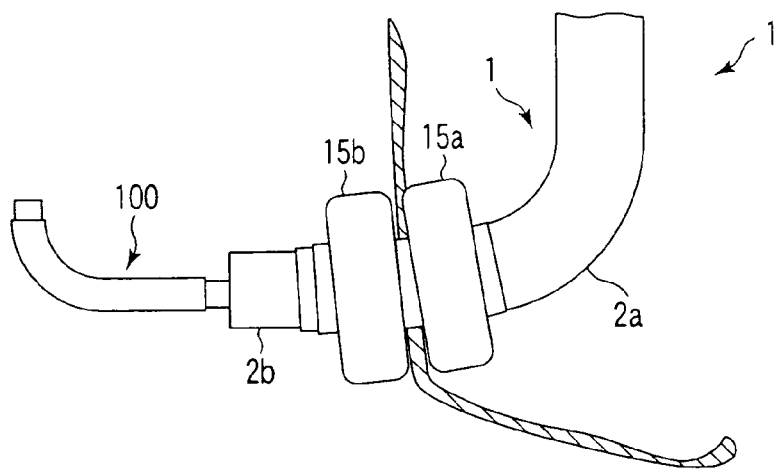
FIGS. 22 to 24 are schematic diagrams showing the vicinity of a distal end of the guide tube shown in FIG. 17 in order to explain an observation or a therapeutic treatment of an abdominal cavity using the guide tube.
Figure 24:
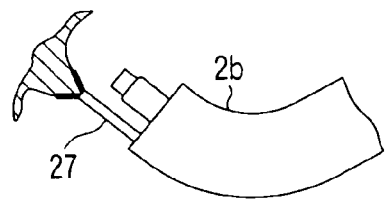

The operation of the guide tube 1 according to the third embodiment will now be described with reference to FIGS. 22 to 24.

According to the present embodiment, the guide tube 1 has previously covered the endoscope 100 such as a gastroendoscope. After the endoscope 100 is inserted into a stomach through the mouth, the guide tube 1 is advanced along the endoscope 100 and the distal end of the guide tube 1 is inserted into the stomach. Subsequently, in a manner similar to the first and second embodiments, a perforation is formed at a desired portion in the stomach wall 80 and the balloons 15a and 15b are then expanded, so that the guide tube 1 is fixed to the stomach wall 80 (FIG. 22). In this instance, when the endoscope 100 and the inner-tube module 2b are advanced from the outer-tube module 2a, the distal end of the endoscope 100 and the distal end of the inner-tube module 2b are projected from the stomach into the abdominal cavity.

Figure 23:
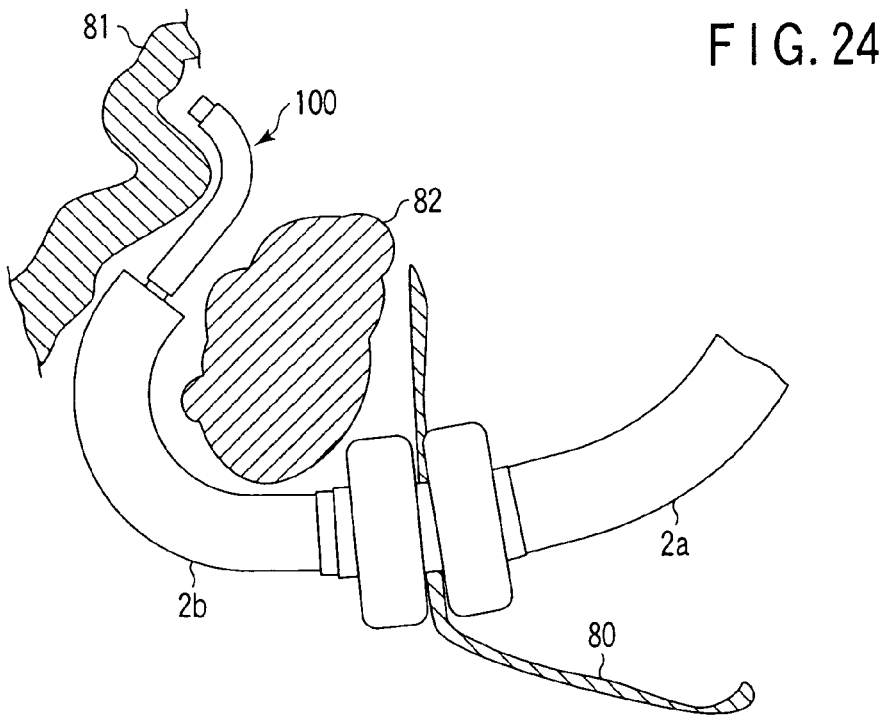

As shown in FIG. 23, when the angle control section 16 on the operating handle 6 is operated with respect to the inner-tube module 2b to pull the operating wire 18, the width of each of the slits 25 on the inner-tube module 2b is narrowed. Consequently, the inner-tube module 2b is bent and the endoscope 100 is then guided to a desired portion in, for example, an intestine 81 to conduct a diagnosis thereon. Subsequently, as shown in FIG. 24, a forceps 27 is inserted into the forceps channel 22 from the forceps orifice 26 and is then protruded from the distal end of the inner-tube module 2b, so that a required therapeutic treatment for the intestine 81 can be performed. The other operation is the same as those of the first and second embodiments.

According to the present embodiment, in addition to the advantages of the first and second embodiments, in the guide tube 1, the outer-tube module 2a and the inner-tube module 2b can be moved mutually in the axial direction and the inner-tube module 2b has the bending function. Accordingly, even when the desired intestine 81 exists away from the perforation in the stomach wall, the endoscope 100 can be guided by the guide tube 1. Furthermore, since the guide tube 1 has the forceps channel 22, the therapeutic treatment and the operation can be performed independently of the endoscope 100.

FIGS. 25 to 33 show a fourth embodiment of the present invention.

Figure 25:
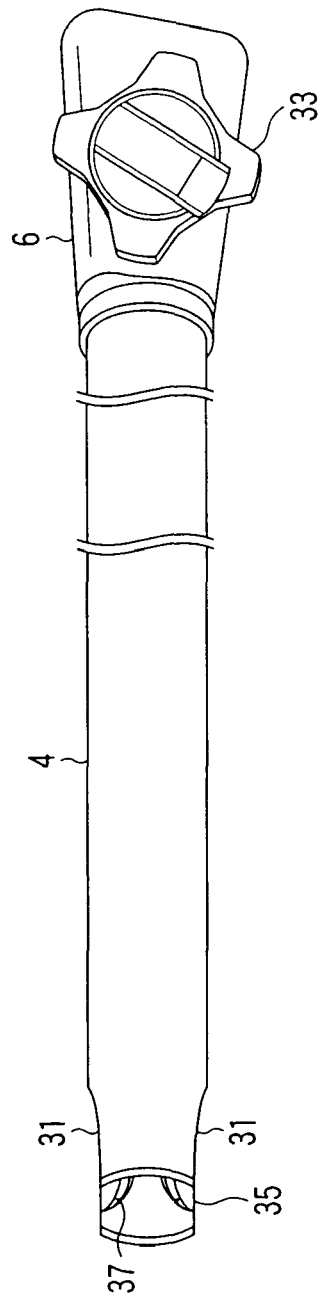
FIG. 25 is a perspective view for explaining the entire constitution of a guide tube according to a fourth embodiment.

According to the present embodiment, as shown in FIG. 25, the endoscope guide tube 1, which is inserted through the mouth and stomach wall to conduct a diagnosis and a therapeutic treatment, has a flexible tubular main body 4. At least one slit 31 is formed at the distal end of the tubular main body 4. Preferably, two slits 31 facing each other in the radial direction are formed. In the inner bore at the distal end of the guide tube 1, both ends of a pair of shafts 36 facing in the transverse axis perpendicular to the longitudinal axis of the guide tube 1 are fixed to the tubular main body 4. The pair of shafts are arranged substantially in parallel to each other so as to face each other. A rotatable pulley 39 is rotatably provided for the periphery of each shaft 36. A curved needle 35 having a bent and sharp edge is attached to each pulley 39. The curved needle 35 has a concave hook 37 in the vicinity of the edge thereof. The edge slit 31 is disposed in such a manner that when the curved needle 35 is rotated round the shaft 36, the slit 31 has no interference with the wall of the tubular main body 4. Further, the end of a needle operating wire 38 is connected to each pulley 39 and is then wounded around the pulley 39 in order to transmit a driving force from the proximal end of the guide tube 1 to the curved needle 35. The other end of each needle operating wire 38 is slidably inserted into the small bore of the tubular main body 4 and is then connected to a needle control section 33 on the operating handle 6 at the proximal end.

Referring to FIGS. 26 to 33, the operation to fix the endoscope guide tube 1 according to the present embodiment to the stomach wall, conduct a diagnosis on an abdominal cavity, and suture and close a perforation will now be described.

Figure 26:
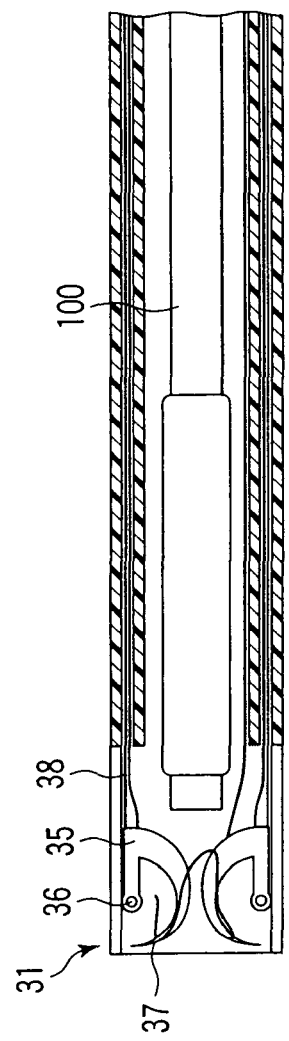
FIG. 26 is a sectional view of the vicinity of a distal end of the guide tube shown in FIG. 25.
Figure 27:
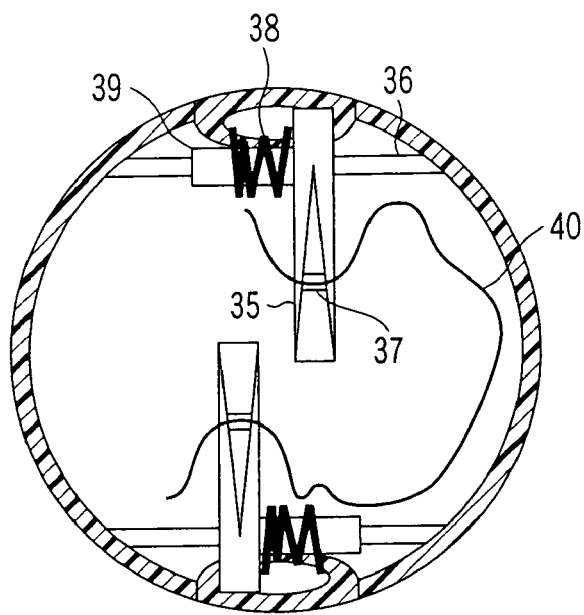
FIG. 27 is an external view of the distal end of the guide tube shown in FIG. 25 as observed from the front side.
Figure 28:
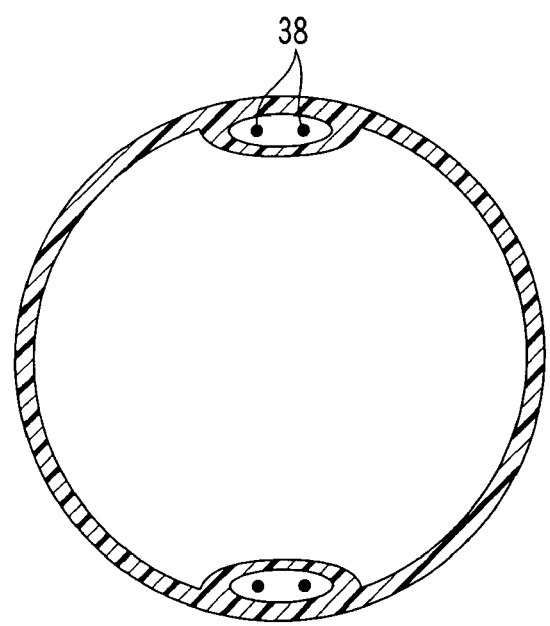
FIG. 28 is a cross-sectional view of a shaft section of the guide tube shown in FIG. 25.

As shown in FIGS. 26 and 27, one end of a suture thread 40 is set to a free end, the intermediate portion of the thread is engaged between the hooks 37 of the two curved needles 35, and the other end is withdrawn from an orifice (not shown) at the proximal end to the outside through the inner bore of the tubular main body 4. After that, while the curved needle 35 is withdrawn in the inner bore of the tubular main body 4, the guide tube 1 is advanced through the mouth and is then inserted into the stomach. Subsequently, a perforation in the stomach wall 80 and the enlargement of the perforation can be performed in a manner similar to the first embodiment.

Figure 29:
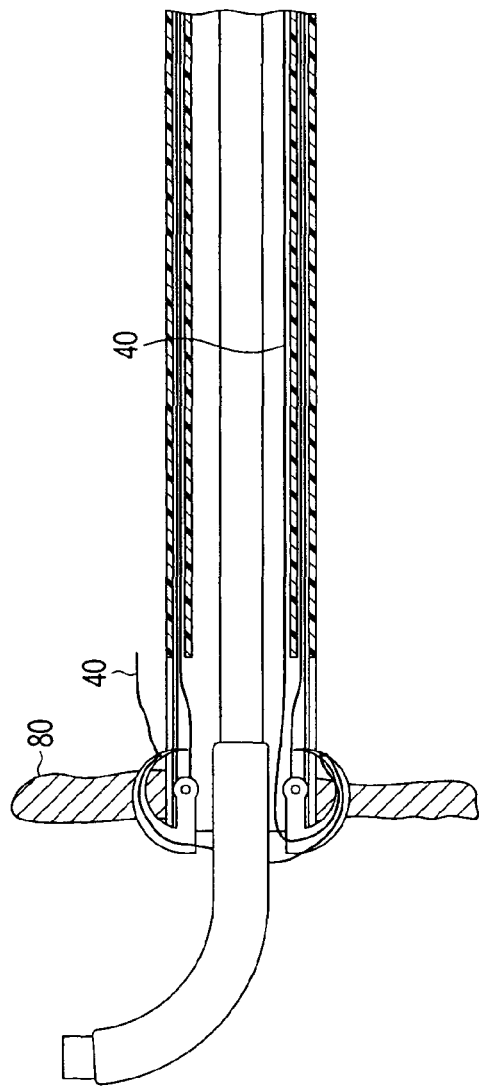

Subsequently, while the distal end of the guide tube 1 is inserted into the perforation, the needle control section 33 is rotated to slide the two needle operating wires 38 forward or backward. The pulley 39 and the curved needle 35 connected to each needle operating wire 38 are rotated, so that the curved needle 35 is projected on the periphery as shown in FIG. 29 to pierce into the stomach wall 80. Consequently, the distal end of the guide tube 1 is fixed to the stomach wall 80. Since the curved needle 35 is moved on the periphery, a large space is formed in the inner bore at the distal end of the tubular main body 4. Subsequently, when the endoscope 100 is advanced as shown in FIG. 29, the endoscope 100 is projected from the distal end of the tubular main body 4, so that the endoscope 100 reaches the abdominal cavity. In this state, the diagnosis of the abdominal cavity is conducted.

Figure 30:
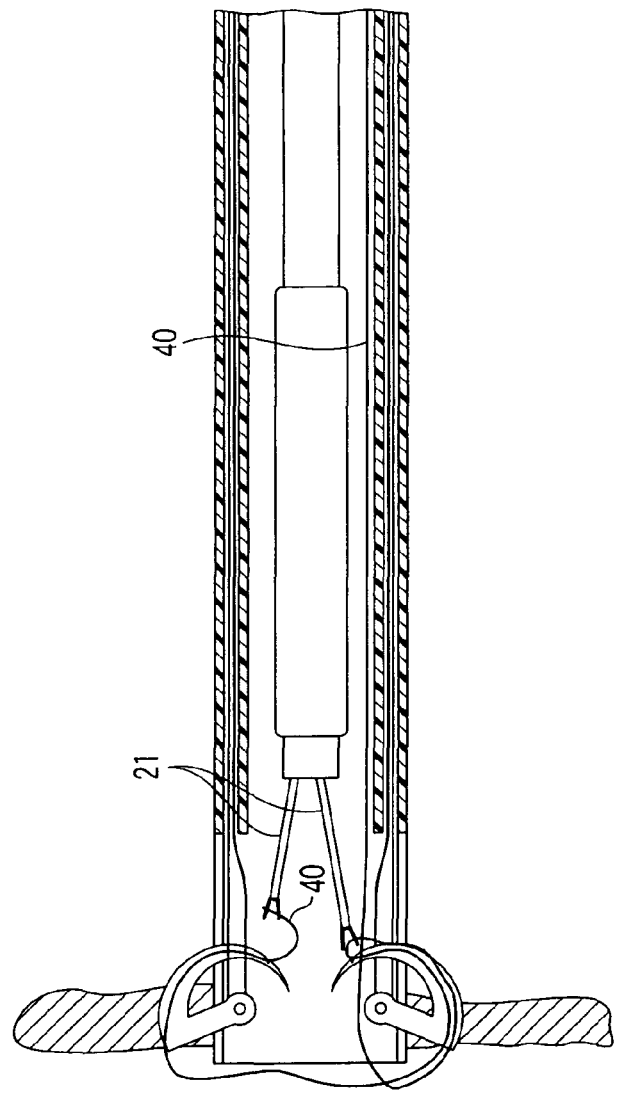
Figure 33:
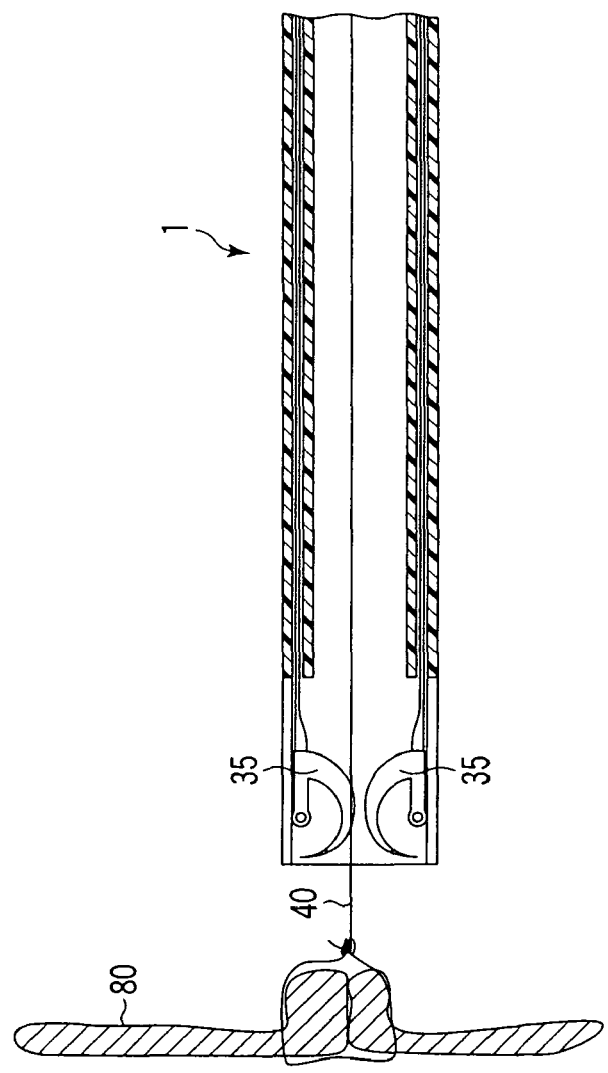

Subsequently, as shown in FIG. 30, the endoscope 100 is retracted toward the proximal end and the needle control section 33 is then operated to rotate the curved needles, namely, the pulleys 39 until the hooks 37 are received in the inner bore of the tubular main body 4. In this state, the grasping forceps 21 inserted through the endoscope channel (not shown) in the endoscope 100 are projected into the inner bore of the tubular main body 4 to grasp the suture thread 40 at the edges of the curved needles 35. Subsequently, the needle control section 33 is rotated in the reverse direction to withdraw the curved needles 35 from the stomach wall 80. After that, the grasping forceps 21 grasping the suture thread 40 are withdrawn toward the proximal end as shown in FIGS. 31 and 32, whereby both ends of the suture thread 40 are withdrawn from the body cavity through the opening (not shown) on the operating handle 6. Subsequently, both the ends of the suture thread 40 are operated to form a clinch knot and one end of the thread is pulled to transfer the knot to the distal end. Consequently, the diameter of a loop of the suture thread 40 penetrating the stomach wall 80 is reduced to suture and close the perforation in the stomach wall 80 as shown in FIG. 33.

Finally, the endoscope 100 is again inserted into the guide tube 1. While the sutured portion is being observed, a cutting forceps, which is inserted through the endoscope channel (not shown) in the endoscope 100 and is projected from the distal end of the endoscope 100, is operated to cut the suture thread 40. Consequently, the suturing and closing operation is finished.

According the present embodiment, the guide tube 1 has advantages in that the guide tube 1 is surely fixed to the stomach wall 80 and, further, the closing operation can be easily performed.

FIGS. 34 to 43 show a fifth embodiment of the present invention.

Figure 34:
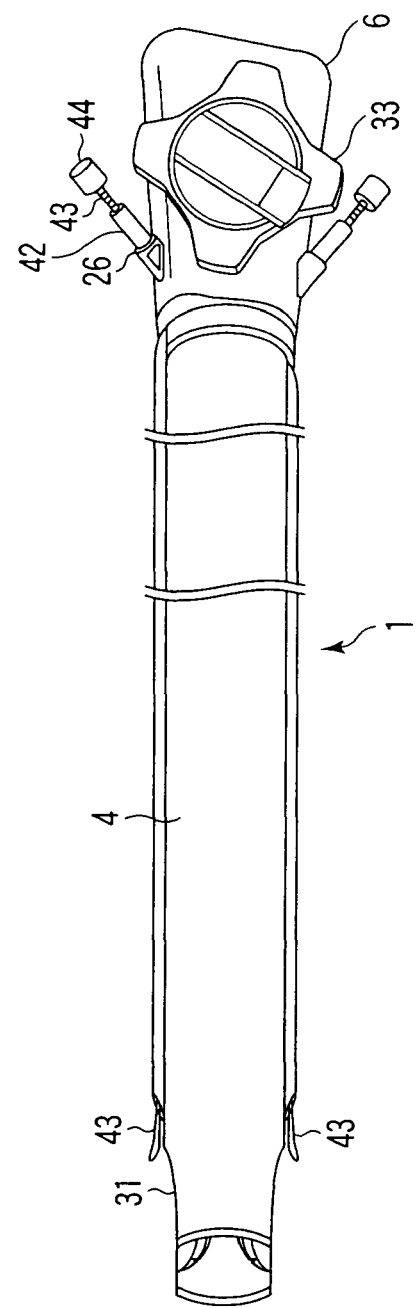
FIG. 34 is a perspective view for explaining the entire constitution of a guide tube according to a fifth embodiment.
Figure 35:
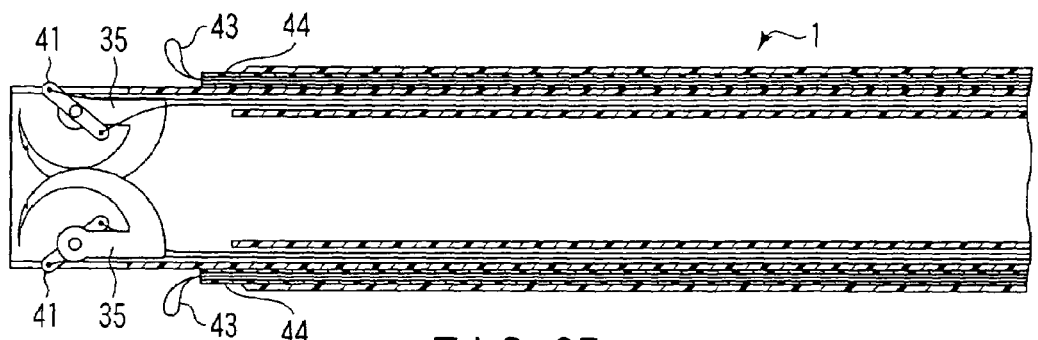
FIG. 35 is a sectional view showing the vicinity of a distal end of the guide tube in FIG. 34.

As shown FIGS. 35 to 38, a pair of snare lumens 45, which are preferably arranged so as to face each other in the radial direction, are integrally provided for the tubular main body 4. As shown in FIGS. 34 and 35, a distal end of each snare lumen 45 is opened at the proximal end of each tip slit 31 and a proximal end thereof communicates with the forceps opening 26 on the operating handle 6. A flexible snare tube 42 enclosing a snare wire 43, whose end is a loop, is inserted into each snare lumen 45 so that the snare tube 42 can be inserted or withdrawn into/from the snare lumen 45. A proximal end of each snare tube 42 is projected from the forceps opening 26 and, further, the snare wire 43 is projected from the proximal end of the snare tube 42. A proximal end of the snare wire 43 is connected to a handle 44 (FIG. 34).

Figure 36:
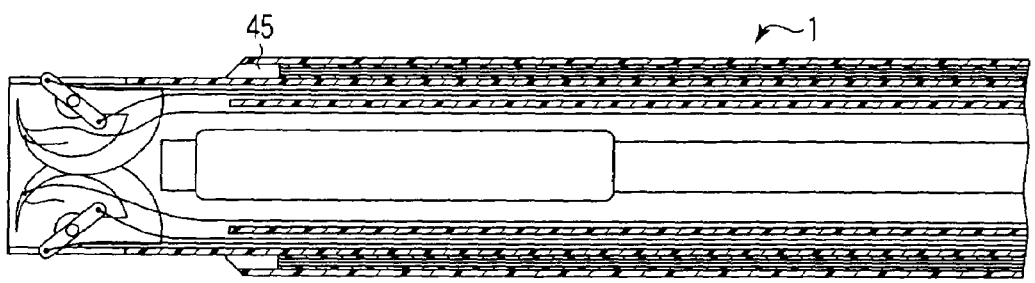
FIG. 36 is a sectional view showing the vicinity of the distal end engaged with a suture thread.
Figure 37:
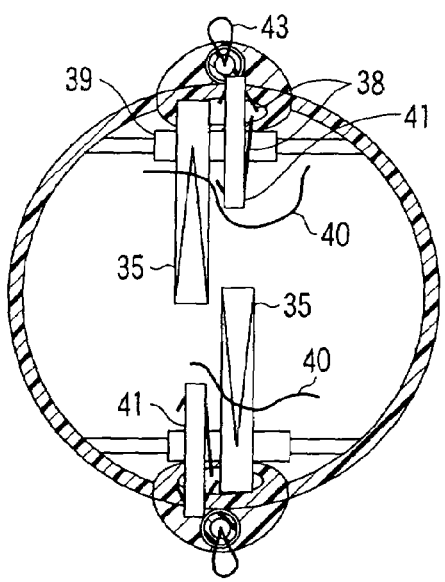
FIG. 37 is an explanatory diagram of the distal end in FIG. 36 as observed from the front side.
Figure 38:
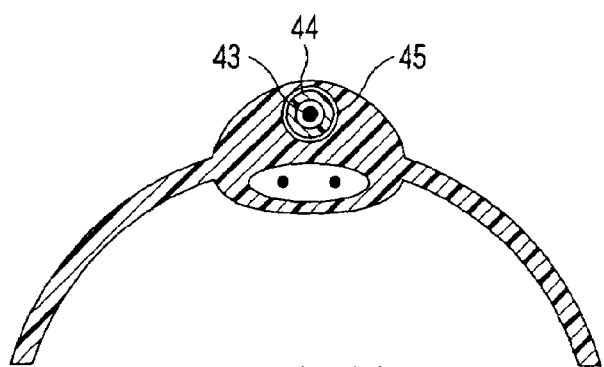
FIG. 38 is a cross-sectional view showing an enlarged portion of a tubular main body.
Figure 41:
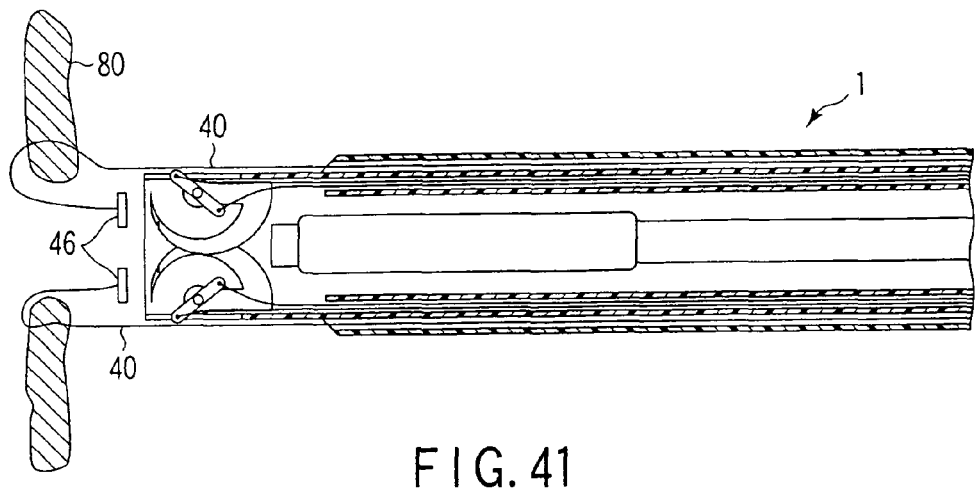
Figure 42:
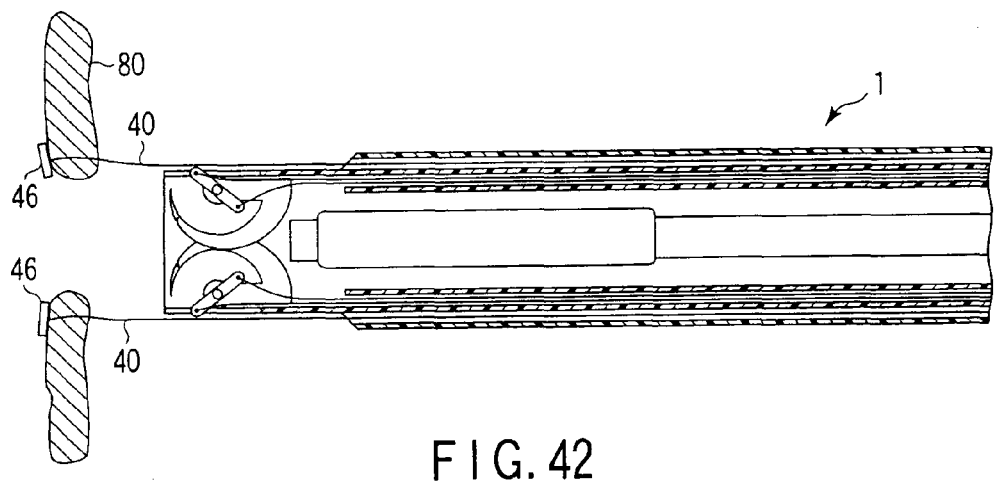

As shown FIGS. 35 and 36, the center portion of a link 41 is fixed to each pulley 39. The ends of the needle operating wires 38 are connected to both ends of each link 41 so that the link can be rotated.

The operation of the guide tube 1 according to the fifth embodiment will now be described with reference to FIGS. 36 and 39 to 43.

First, the suture thread 40 having an engaging portion 46 (refer to FIGS. 41 and 42) at one end is engaged with each curved needle 35 in a manner similar to the fourth embodiment. The distal end of the guide tube 1 is inserted into the perforation of the stomach wall 80 in the same way as the fourth embodiment. Subsequently, the needle operating wires 38 are slit forward and backward by rotating the needle control section 33. The link 41 fixed to the end of each needle operating wire 38 is rotated around the shaft 36 and each curved needle 35 is pierced into the stomach wall 80, so that the guide tube 1 is fixed to the stomach wall 80. The subsequent diagnosis and therapeutic treatment are the same as those of the fourth embodiment.

Subsequently, as shown in FIG. 39, when each snare tube 42 is advanced, the snare tube 42 is projected from the orifice at the distal end of each snare lumen 45. Further, each snare wire 43 is advanced to open the loop at the distal end of the snare wire 43 projected from the orifice at the distal end of the snare tube 42. Each snare tube 42 and each snare wire 43 are operated so as to move forward and backward, whereby the suture thread 40 is disposed in the loop of each snare wire 43. In this state, when each snare tube 42 is advanced, the suture thread 40 is sandwiched between the snare tube 42 and the snare wire 43 and is then fixed.

Subsequently, the needle control section 33 is rotated to withdraw the curved needles 35 from the stomach wall 80. When the snare tubes 42 and the snare wires 43 are withdrawn toward the proximal end and are then removed from the forceps orifices 26, the free ends of the suture threads 40 are withdrawn from the body cavity. Further, when the suture threads 40 are pulled toward the proximal end, the engaging portions 46 at the other ends of the suture threads 40 are sent into the stomach wall 80 (refer to FIGS. 41 and 42).

Figure 43:
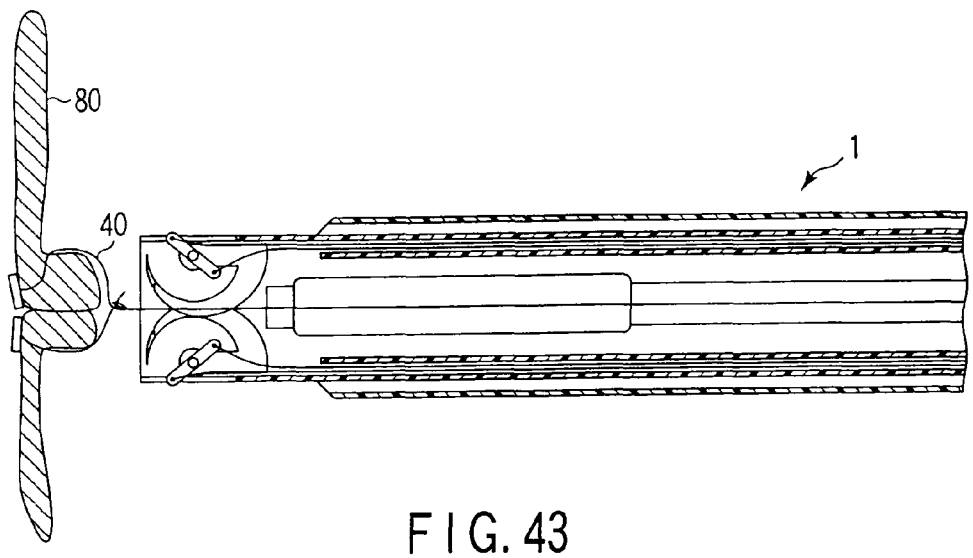

Subsequently, the guide tube 1 is withdrawn from the body wall and the guide tube 1 and the endoscope 100 are again inserted into the stomach along the suture threads 40. The ends of the suture threads 40 withdrawn from the body cavity are ligatured in the same way as the fourth embodiment and the knot is transferred, whereby the suturing and closing operation of the perforation in the stomach wall 80 is completed (FIG. 43).

According to the present embodiment, in addition to the advantages of the fourth embodiment, since the rotation driving section for the curved needle 35 comprises the link 41, the curved needle 35 can have a larger rotation torque. The piercing operation of the curved needle 35 can be easily performed. Furthermore, since the guide tube 1 has the snare tubes 42 and the snare wires 43 as means for grasping the suture threads 40, the suturing and closing operation can be performed irrespective of the presence or absence of the forceps channel in the endoscope 100.

As mentioned above, the present invention has been described in relation to the preferred embodiments shown in the drawings. Other embodiments can be made without departing from the spirit of the present invention. A modification can be added to the foregoing embodiments in order to realize the same function as that of the present invention. Accordingly, the present invention is not limited to any one of the embodiments and various combinations can be made within the spirit and scope of the present invention.

What is claimed is:

1. A flexible guide tube to guide an endoscope or a therapeutic device into a body cavity through the mouth, the guide tube comprising:
    an insertion section which can be inserted into a body through the mouth, the insertion section having a distal end arranged in the body and at least one lumen, through which the endoscope or therapeutic device can be inserted;
    a proximal end which is connected to the insertion section and is arranged on the outside of the body;
    a shaft which is arranged in the vicinity of the distal end in the direction perpendicular to the direction in which the longitudinal axis of the insertion section extends;
    a curved needle which is rotatably attached to the shaft and which has an engaging portion capable of engaging a suture therewith; and
    driving force transmitting member which has one end connected to the curved needle and the other end arranged at the proximal end,
    wherein the distal end is capable of being fixed to a required portion in the body cavity to suture tissue by operating the driving force transmitting member on the outside of the body.

2. The guide tube according to claim 1, further comprising:
    at least one grasping means arranged closer to the proximal end than the curved needle.

* * * * *